United States Patent
Hersh et al.

(10) Patent No.: US 8,556,821 B2
(45) Date of Patent: Oct. 15, 2013

(54) ADAPTIVE FREQUENCY DOMAIN FILTERING FOR IMPROVED NON-INVASIVE BLOOD PRESSURE ESTIMATION

(75) Inventors: Lawrence T. Hersh, Tamp, FL (US); Sai Kolluri, Tamp, FL (US); Robert F. Donehoo, Lutz, FL (US)

(73) Assignee: General Electric Company, Schenectady, NY (US)

( * ) Notice: Subject to any disclaimer, the term of this patent is extended or adjusted under 35 U.S.C. 154(b) by 1118 days.

(21) Appl. No.: 12/034,143

(22) Filed: Feb. 20, 2008

(65) Prior Publication Data

US 2009/0209868 A1 Aug. 20, 2009

(51) Int. Cl.
*A61B 5/22* (2006.01)

(52) U.S. Cl.
USPC .......................................... 600/490

(58) Field of Classification Search
None
See application file for complete search history.

(56) References Cited

U.S. PATENT DOCUMENTS

| | | | |
|---|---|---|---|
| 5,913,826 A * | 6/1999 | Blank | 600/500 |
| 6,050,951 A * | 4/2000 | Friedman et al. | 600/485 |
| 6,348,038 B1 * | 2/2002 | Band et al. | 600/485 |
| 2003/0233204 A1 * | 12/2003 | Peel et al. | 702/104 |
| 2005/0143634 A1 * | 6/2005 | Baker et al. | 600/310 |
| 2006/0122476 A1 * | 6/2006 | Van Slyke | 600/336 |
| 2007/0106162 A1 * | 5/2007 | Illyes et al. | 600/481 |
| 2007/0288103 A1 * | 12/2007 | Choudhury et al. | 700/35 |
| 2008/0281168 A1 * | 11/2008 | Gibson et al. | 600/301 |
| 2009/0306487 A1 * | 12/2009 | Crowe et al. | 600/322 |

* cited by examiner

*Primary Examiner* — N. C. Yang
*Assistant Examiner* — Richard Moerschell
(74) *Attorney, Agent, or Firm* — Andrus, Sceales, Starke & Sawall, LLP

(57) ABSTRACT

A system for processing oscillometric data from a plurality of pressure steps to determine the blood pressure of a patient as disclosed herein. A heart rate monitor connected to the patient acquires the patient's heart rate. A time to frequency domain converter receives oscillometric data and converts the oscillometric data into the frequency domain. A harmonic frequency calculator is connected to the heart rate monitor and derives at least the heart rate fundamental frequency. A filter connected to the time to frequency domain converter and the harmonic frequency calculator that produces a filter frequency domain oscillometric signal. A reconstruction calculator receives the filtered frequency domain oscillometric signal and reconstructs a time domain oscillometric signal. A method of computing an oscillometric envelope for use in determining the blood pressure of a patient is also disclosed herein.

18 Claims, 8 Drawing Sheets

ADAPTIVE FREQUENCY DOMAIN FILTERING FOR IMPROVED NON-INVASIVE BLOOD PRESSURE ESTIMATION

FIELD OF THE DISCLOSURE

The present disclosure is related to the field of non-invasive blood pressure monitoring. More specifically, the present disclosure relates to adaptive filtering techniques for the improved processing of artifact contaminated oscillometric data.

BACKGROUND

The human heart periodically contracts to force blood through the arteries. As a result of this pumping action, pressure pulses or oscillations exist in these arteries and cause them to cyclically change volume. The minimum pressure during each cycle is known as the diastolic pressure and the maximum pressure during each cycle is known as the systolic pressure. A further pressure value, known as the "mean arterial pressure" (MAP) represents a time-weighted average of the measured blood pressure over each cycle.

While many techniques are available for the determination of the diastolic, systolic, and mean atrial pressures of a patient, one such method typically used in non-invasive blood pressure monitoring is referred to as the oscillometric technique. This method of measuring blood pressure involves applying an inflatable cuff around an extremity of a patient's body, such as the patient's upper arm. The cuff is then inflated to a pressure above the patient's systolic pressure and then incrementally reduced in a series of small steps. A pressure sensor pneumatically connected to the cuff measures the cuff pressure throughout the deflation process. The sensitivity of the sensor is such that it is capable of measuring the pressure fluctuations occurring within the cuff due to blood flowing through the patient's arteries. With each beat, blood flow causes small changes in the artery volume which are transferred to the inflated cuff, further causing slight pressure variations within the cuff which are then detected by the pressure sensor. The pressure sensor produces an electrical signal representing the cuff pressure level combined with a series of small periodic pressure variations associated with the beats of a patient's heart for each pressure step during the deflation process. It has been found that these variations, called "complexes" or "oscillations," have a peak-to-peak amplitude which is minimal for applied cuff pressures above the systolic pressure. As the cuff pressure is decreased, the oscillation size begins to monotonically grow and eventually reaches a maximum amplitude. After the oscillation size reaches the maximum amplitude, the oscillation size decreases monotonically as the cuff pressure continues to decrease. Oscillametric data such as this is often described as having a "bell curve" appearance. Indeed, a best-fit curve, or envelope, may be calculated representing the measured oscillometric pulses. Physiologically, the cuff pressure at the maximum oscillation amplitude value approximates the MAP. In addition, complex amplitudes at cuff pressures equivalent to the systolic and diastolic pressures have a fixed relationship to this maximum oscillation amplitude value. Thus, the oscillometric method is based upon measurements of detected oscillation amplitudes at various cuff pressures.

Blood pressure measuring devices operating according to the oscillometric method detect the amplitude of the pressure oscillations at various applied cuff pressure levels. The amplitudes of these oscillations, as well as the applied cuff pressure, are stored together as the device automatically changes the cuff pressures through a predetermined pressure pattern. These oscillation amplitudes define an oscillometric "envelope" and are evaluated to find the maximum value and its related cuff pressure, which is approximately equal to MAP. The cuff pressure below the MAP value which produces an oscillation amplitude having a certain fixed relationship to the maximum value is designated as the diastolic pressure, and, likewise, the cuff pressures above the MAP value which results in complexes having an amplitude with a certain fixed relationship to that maximum value is designated as the systolic pressure. The relationships of oscillation amplitude at systolic and diastolic pressures, respectively, to the maximum value at MAP are empirically derived ratios depending on the preferences of those of ordinary skill in the art. Generally, these ratios are designated in the range of 40%-80% of the amplitude at MAP.

One way to determine oscillation magnitudes is to computationally fit a curve to the recorded oscillation amplitudes and corresponding cuff pressure levels. The fitted curve may then be used to compute an approximation of the MAP, systolic, and diastolic data points. An estimate of MAP is taken as the cuff pressure level with the maximum oscillation. One possible estimate of MAP may therefore be determined by finding the point on the fitted curve where the first derivative equals zero. From this maximum oscillation value data point, the amplitudes of the oscillations at the systolic and diastolic pressures may be computed by taking a percentage of the oscillation amplitude at MAP. In this manner, the systolic data point and the diastolic data point along the fitted curve may each be computed and therefore their respective pressures may also be estimated. This curve fitting technique has the advantage of filtering or smoothing the raw oscillometric data. However, in some circumstances it is been found that additional filtering techniques used to build and process the oscillometric envelope could improve the accuracy of the determination of the blood pressure values.

The reliability and repeatability of blood pressure computations hinges on the ability to accurately determine the oscillation amplitude. However, the determination of the oscillation amplitudes is susceptible to artifact contamination. As the oscillometric method is dependent upon detecting tiny fluctuations in measured cuff pressure, outside forces affecting this cuff pressure may produce artifacts that in some cases may completely mask or otherwise render the oscillometric data useless. One such source of artifacts is from voluntary or involuntary motion by the patient. Involuntary movements such as the patient shivering may produce high frequency artifacts in the oscillometric data. Voluntary motion artifacts, such as those caused by the patient moving his or her arm, hand, or torso, may produce low frequency artifacts.

Presently available systems may be able to determine whether or not collected oscillometric data has been corrupted with artifact; however, current filtering techniques are ineffective at removing artifacts that have similar frequency content as the desired oscillometric data. Alternatively, non-invasive blood pressure systems may simply reject oscillometric data that has been designated as being corrupted by artifacts. In these instances, more oscillometric data must be collected at each pressure step until reasonably artifact free oscillometric data may be acquired. This may greatly lengthen the time for determination of a patient's blood pressure and submit the patient to increased discomfort that is associated with the inflatable cuff restricting blood flow to the associated extremity.

BRIEF DISCLOSURE

A method of computing an oscillometric envelope for use in determining the blood pressure of a patient is disclosed herein. The method may include the steps of receiving an oscillometric signal and an indication of a patient's heart rate. Next, the fundamental frequency and at least one harmonic frequency of the heart rate are computed. The oscillometric data is then converted to the frequency domain. The frequency domain oscillometric signal is then filtered at the heart rate fundamental frequency and at least one harmonic frequency. Next, the oscillometric signal may be reconstructed from the filtered frequency domain signals to produce a reconstructed oscillometric signal. Finally, an oscillometric envelope data point may be determined from the reconstructed oscillometric signal.

Still further disclosed herein is a system for processing oscillometric data from a plurality of pressure steps of a blood pressure cuff to determine the blood pressure of a patient. The system may include a heart rate monitor connected to the patient. The heart rate monitor acquires the patient's heart rate at each pressure step. A time to frequency domain converter receives the oscillometric data acquired at each pressure step and converts the oscillometric data to the frequency domain. A harmonic frequency calculator is connected to the heart rate monitor and the harmonic frequency calculator derives at least the heart rate fundamental frequency. A filter connected to the time-to-frequency domain converter and the harmonic frequency calculator produces filtered frequency domain oscillometric data. A reconstruction calculator receives the filtered frequency domain oscillometric data and reconstructs a time domain oscillometric signal from the filtered frequency domain oscillometric data. An oscillometric envelope calculator processes the time domain oscillometric signal at each pressure step to produce an oscillometric envelope from envelope data points corresponding to each pressure step. A blood pressure determination calculator is connected to the oscillometric envelope calculator and analyzes the oscillometric envelope to determine the blood pressure of the patient.

DETAILED DISCLOSURE

Figure 1:
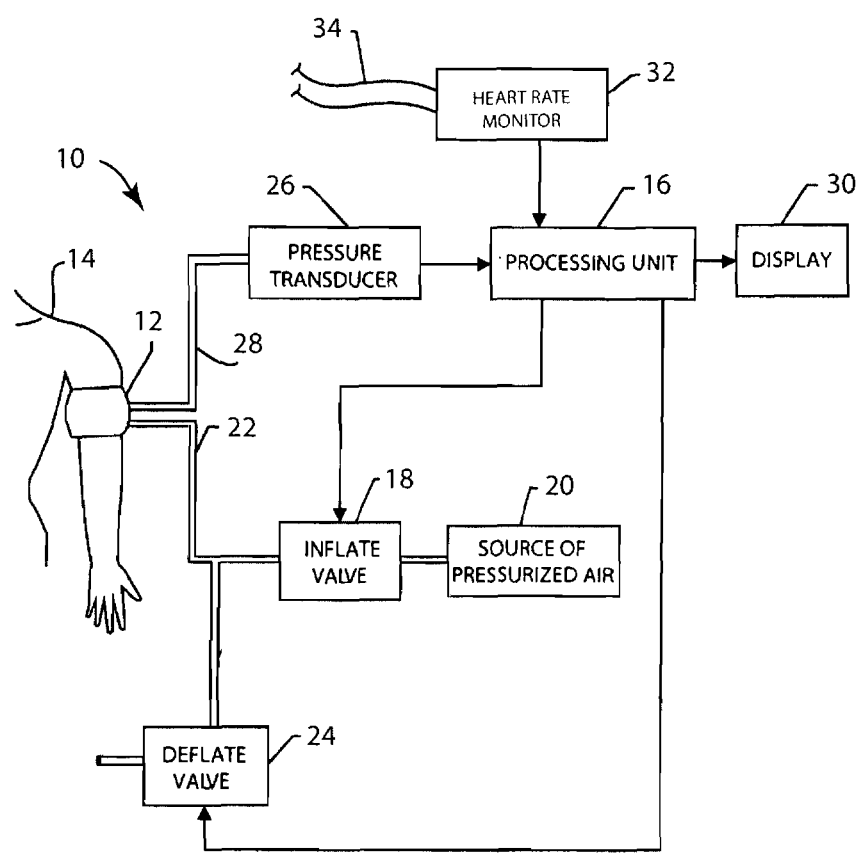
FIG. 1 depicts an embodiment of a system for the non-invasive measurement of blood pressure.

FIG. 1 depicts an embodiment of a non-invasive blood pressure (NIBP) monitoring system 10. The NIBP monitoring system 10 includes a pressure cuff 12 that is a conventional flexible, inflatable and deflatable cuff worn on the arm or other extremity of a patient 14. A processing unit 16 controls an inflate valve 18 that is disposed between a source of pressurized air 20 and a pressure conduit 22. As the inflate valve 18 is controlled to increase the pressure in the cuff 12, the cuff 12 constricts around the arm of the patient 14. Upon reaching a sufficient amount of pressure within the cuff 12, the cuff 12 fully occludes the brachial artery of the patient 14.

After the cuff 12 has been fully inflated, the processing unit 16 further controls a deflate valve 24 to begin incrementally releasing pressure from the cuff 12 back through pressure conduit 22 and out to the ambient air. During the inflation and incremental deflation of the cuff 12, a pressure transducer 26, pneumatically connected to the pressure cuff 12 by pressure conduit 28 measures the pressure within the pressure cuff 12. In an alternative embodiment, the cuff 12 is continuously deflated as opposed to incrementally deflated. In such continuously deflating embodiments, the pressure transducer 26 may measure the pressure within the cuff continuously or incrementally at regular intervals.

As the pressure within the cuff 12 decreases, the pressure transducer 26 will detect oscillometric pulses in the measured cuff pressure that are representative of the pressure fluctuations caused by the patient's blood flowing into the brachial artery with each heart beat and the resulting expansion of the artery to accommodate the additional volume of blood.

The cuff pressure data as measured by the pressure transducer 26, including the oscillometric pulses, is provided to the processing unit 16 such that the cuff pressure data may be processed and analyzed and a determination of the patient's blood pressure, including systolic pressure, diastolic pressure and MAP can be displayed to a clinician on a display 30.

The processing unit 16 may further receive an indication of the heart rate of the patient 14 as acquired by a heart rate monitor 32. The heart rate monitor 32 acquires the heart rate of the patient 14 using one or more of a variety of commonly used heart rate detection techniques. One heart rate detection technique that may be used would be that of electrocardiography (ECG) wherein electrical leads 34 connected to specific anatomical locations on the patient 14 monitor the propagation of the electrical activity through the patient's heart. Alternatively, the patient's heart rate may be acquired using $SpO_2$, plethysmography, or other known techniques, including signal processing and analysis of the cuff pressure data.

Figure 2:
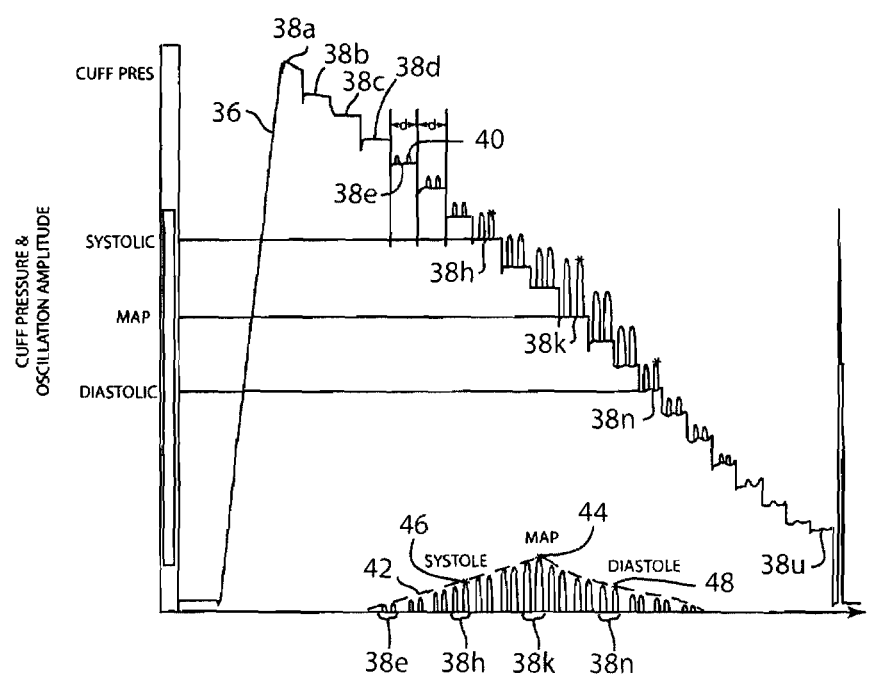
FIG. 2 is a graph depicting the oscillometric data collected from a blood pressure cuff.

FIG. 2 is a graph depicting various pressure values that may be acquired from the NIBP monitoring system 10 depicted in FIG. 1. The cuff pressure as determined by the pressure transducer 26 is represented as cuff pressure graph 36. The cuff pressure peaks at 38a which is the cuff pressure at which the cuff 12 has been fully inflated as controlled by the processing unit 16. The processing unit 16 controls the inflation of the cuff 12 such that 38a is a pressure that is sufficiently above the systolic pressure of the patient. This may be controlled or modified by referencing previously determined values of patient blood pressure data by reference to standard medical practices, or blood pressure estimations. The cuff pressure graph 36 then incrementally lowers at a series of pressure steps 38a-38u which reflect each incremental pressure reduction in the cuff 12 as controlled by the deflate valve 24. Before the cuff pressure has reached a pressure step at which the patient brachial artery is no longer completely occluded, the measured cuff pressure will show oscillometric pulses 40. The number of oscillometric pulses detected at each pressure step is controlled as a function of the heart rate of the patient and the length of time that the NIBP system collects data at each pressure step, but typically cuff pressure data is recorded at each pressure level to obtain at least two oscillometric pulses.

The cuff pressure is measured at each of the pressure step increments, including the oscillometric pulse data until the cuff pressure reaches an increment such that the oscillometric pulses are small enough to completely specify the oscillometric envelope, such as found at pressure increment 38*u*. At this point, the processing unit 16 controls the deflate valve 24 to fully deflate the pressure cuff 12 and the collection of blood pressure data is complete.

FIG. 2 further depicts an oscillometric envelope 42 as calculated using the oscillometric pulse data collected from the series of incremental cuff pressure steps. The processing unit 16 isolates the oscillometric pulses at each pressure step, and creates a best fit curve to represent the oscillometric envelope 42. The oscillometric envelope is useful in estimating systolic pressure, diastolic pressure and MAP. The MAP 44 is determined as the pressure step increment 38*k* that corresponds to the peak 44 of the oscillometric envelope 42. Once the MAP has been determined, the systolic pressure 46 and diastolic pressure 48 may be identified as the pressure level values associated with particular oscillation amplitudes that are predetermined percentages of the oscillation amplitude at the MAP pressure level. In one embodiment, the systolic pressure 46 corresponds to pressure increment 38*h* where the oscillometric envelope amplitude is 50% that of the MAP. In another embodiment, the diastolic pressure 48 correlates to pressure increment 38*n* where the envelope amplitude is between 60% and 70% that of the envelope amplitude at MAP. The percentages of the MAP amplitude used to estimate the systolic pressure and the diastolic pressure are usually between 40% and 80% depending upon the specific algorithm used by the processing unit 16.

In an alternative embodiment, the amplitude of the oscillometric pulses at each pressure step are averaged to produce an oscillometric envelope data point. In some of these embodiments, techniques such as pulse matching or the elimination of the first and/or last oscillometric pulse at a pressure step may be used to improve the quality of the computed oscillometric data point. The oscillometric envelope 42 may also be created by using the average of the complex amplitudes at the pressure step as the input data points for a best-fit curve. Alternatively, data points of the oscillometric envelope 42 may be the maximum amplitude of the oscillometric pulses at each pressure step.

As can be seen, from FIG. 2, the oscillometric pulses are relatively small with respect to the overall cuff pressure and the pressure increment steps. This makes the detection of the oscillometric pulses highly susceptible to noise and other artifacts. While relatively high frequency noise, such as 60 Hz electromagnetic noise, can be filtered easily, the relatively small size of the oscillometric pulses makes it difficult to adequately filter artifacts due to human motion since these artifacts are typically at a lower signal frequency, such that the frequency of the artifact is similar to that of the oscillometric pulse signal.

The physiological monitoring system, and method of determining blood pressure as disclosed herein aim to provide improved processing of oscillometric pulse signals to remove artifacts of a similar frequency as the oscillometric pulses. Embodiments as disclosed herein may result in producing a higher quality oscillometric pulse signal when the desired physiological signal and the artifact have specific frequency content properties; this leads to increased accuracy in constructing the oscillometric envelope and computation of the patient blood pressure estimates. FIG. 2 demonstrates an example of acquisition of the oscillometric signals using step deflation; however, other techniques of obtaining the oscillometric signals, such as by continuous deflation, are possible, and the description given here is not meant to limit the usefulness of embodiments as disclosed below with respect to step deflation.

Figure 3:
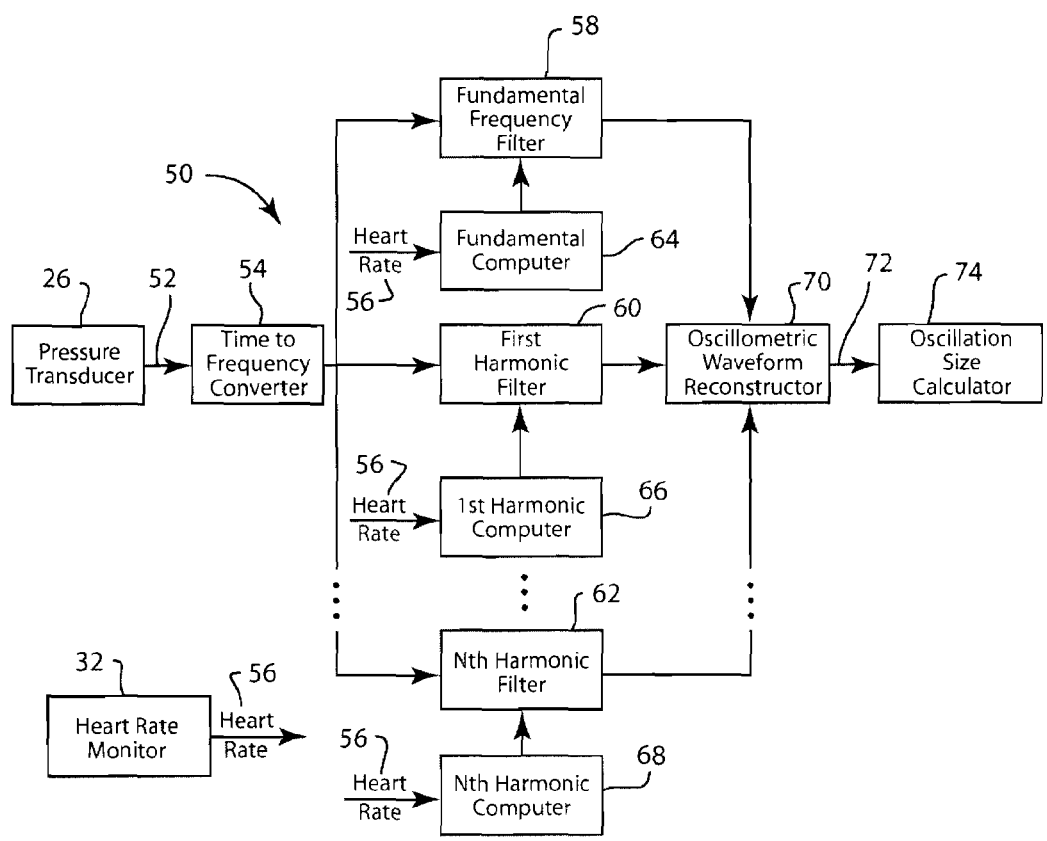
FIG. 3 is an embodiment of a system for the artifact resistant analysis of oscillometric data.

FIG. 3 depicts an embodiment of an oscillometric data processing system 50. The data processing system 50 includes the pressure transducer 26 that collects raw oscillometric pulse signals from the pressure cuff 12. The pressure transducer 26 may sample the cuff pressure at any suitable sampling rate. In one embodiment, the pressure transducer 26 may sample the cuff pressure at a rate of 400 samples per second; however, in other embodiments 100 samples per second or any other sampling rate known to one skilled in the art may be used. In further embodiments, the cuff pressure may be controlled so that each pressure increment step lasts approximately five seconds. However, the length of time of each pressure increment step and alternatively the length of time over which data is recorded for each pressure step may be determined by the sampling rate and the desired resolution for the recorded oscillometric pulses. Therefore, an exemplary embodiment for the purposes of discussion may record 5 seconds of data at a sampling rate of 400 samples per second yielding an oscillometric pulse signal of approximately 2,000 samples for each pressure step. However, it is understood that a wide variety of sampling rates and/or pressure step lengths resulting in oscillometric pulse signals of a different number of samples may be used in alternative embodiments as would be recognized by one skilled in the art.

The raw oscillometric signal 52 is then sent to a time-to-frequency converter 54. The time-to-frequency converter 54 may be a discrete Fourier transform algorithm (DFT). The time-to-frequency converter 54 converts the raw oscillometric signal from a time domain signal into a frequency domain signal. While many techniques are available for this conversion, one such technique would be the application of a 512 point fast Fourier transform (FFT). The size of the FFT may range from 256 points or less to 2048 points or more depending on the sampling rate and the desired output resolution. The result of the time-to-frequency conversion is a signal that expresses the oscillometric signal with respect to its frequencies as opposed to expressing the signal with respect to time. The frequency domain signal is then sent to one or more frequency domain filters. In some cases, depending upon the filtering being required, a full FFT calculation may not be necessary. Certain frequencies or frequency bands may be the only information required. Therefore, in what follows, while the FFT is used as the standard example for the time-to-frequency converter, other more efficient calculations are possible when applying the principles disclosed here.

The data processing system 50 may further include the heart rate monitor 32 that acquires the heart rate of the patient at the time that the raw oscillometric pulse signal was acquired. As previously stated, the heart rate monitor 32 may include ECG or SpO$_2$ techniques; however, in an alternative embodiment the heart rate may be determined from the frequency domain oscillometric signal from the time-to-frequency converter 54. The heart rate 56 is provided to at least one harmonic computer (64, 66, 68) that is associated with a frequency domain filter (58, 64, 62). By using the heart rate to control the frequency domain filtering the oscillometric pulse signal can be optimally obtained even as the heart rate changes from determination to determination or even within a blood pressure determination.

In the data processing system 50, the frequency domain oscillometric signal is provided to a fundamental frequency filter 58, a first harmonic filter 60 and may be provided to any number of additional n$^{th}$ harmonic filters 62. Each of the frequency domain filters is associated with a harmonic computer such as the fundamental frequency computer 64, first harmonic computer 66, and the $n^{th}$ harmonic computer 68, respectively. Each of the harmonic computers (64, 66, 68) receives the patient's heart rate and computes the associated harmonic frequency of the patient's heart rate 56. The frequency domain filters (58, 60, 62) associated to the harmonic computers consist of a band pass filter of a reasonably narrow bandwidth centered at the associated heart rate harmonic. A reasonably narrow bandwidth for each of the pass bands may be a bandwidth less than or equal to the harmonic frequency. In one embodiment, the bandwidth of each of the filters may be 0.6 Hz; however, this is not intended to be limiting on the scope of bandwidths that may be used within the scope of the disclosure.

Figure 5A:
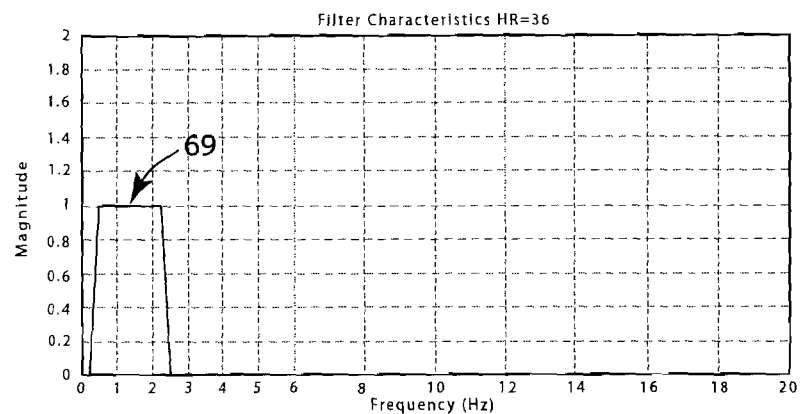
FIGS. 5a-5d are graphs depicting pass band filters adapted to various patient heart rates.
Figure 5B:
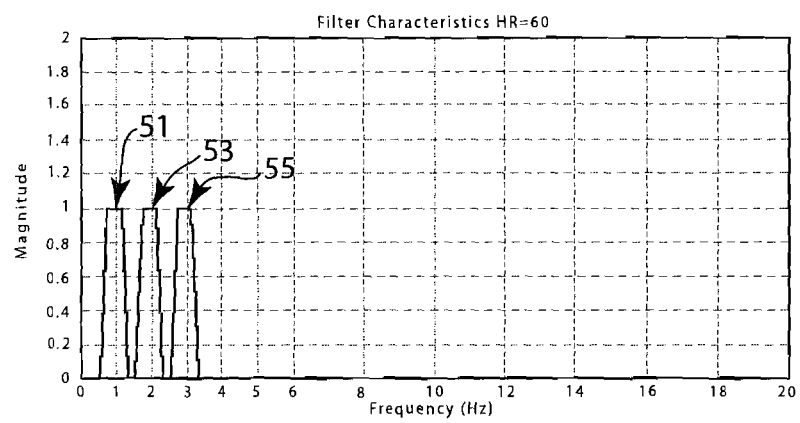
Figure 5C:
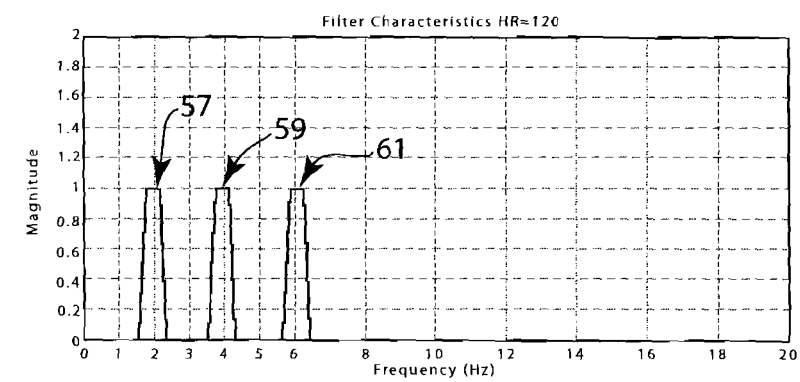
Figure 5D:
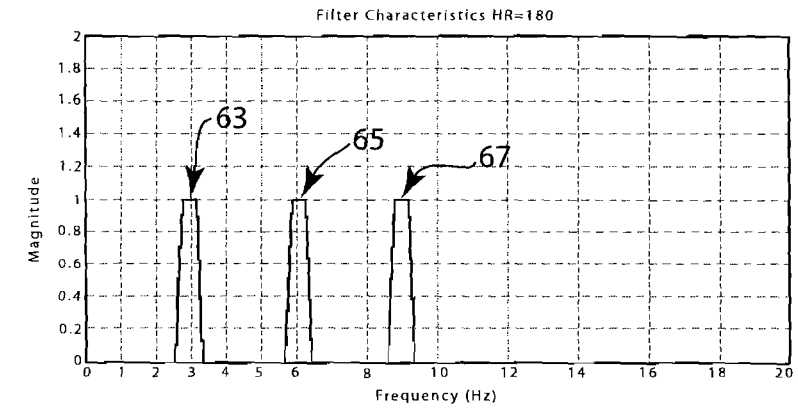

FIGS. 5a-5d depict examples of the adaptive filters that may be applied to the patient ECG data. FIGS. 5b-5d depict exemplary filters at three different heart rates (i.e. 60, 120, 180 BPM). Referring to FIG. 5b, if the patient measured heart rate is 60 BPM then the harmonic computers will compute the fundamental frequency to be 1 Hz, the first harmonic to be at 2 Hz and the second harmonic to be at 3 Hz. Therefore, the filter depicted at FIG. 5b shows a narrow filter pass band 51 centered at the fundamental frequency of 1 Hz. Another filter pass band 53 is centered at the first harmonic 2 Hz and a third pass band 55 is centered at the second harmonic, 3 Hz.

A comparison of the filter depicted in FIG. 5b to the filters depicted in FIGS. 5c and 5d show that as the patient's heart rate changes, the center frequencies of the pass bands of the filters adjust to be centered at the fundamental and harmonic frequencies that coincide with the measured patient's heart rate. Thus, in FIG. 5c a pass band 57 is centered at 2 Hz which is the fundamental frequency of ECG data with a heart rate of 120 BPM. Similarly, pass bands centered at 4 Hz 59 and 6 Hz 61 are centered at the first and second harmonics respectively of the 120 BPM ECG data.

Finally, in FIG. 5d if the patient has a heart rate of 180 BPM, then the ECG data has a fundamental frequency of 3 Hz at which a pass band 63 is located. Another pass band 65 is located at the first harmonic frequency, 6 Hz and a still further pass band 67 is located at the second harmonic, 9 Hz. Thus, as can be seen from a comparison of the filters depicted in FIGS. 5b-5d, substantial amounts of frequency bandwidth wherein noise or other artifacts may occur may be filtered out by adaptively centering pass bands at the specific frequencies at which the cardiac data resides. This type of adaptive filtering can be especially useful when removing low frequency (less than 1 Hz) noise, such as that associated with patient motion artifacts. In those instances wherein the noise artifact is only present at frequencies outside of the adaptive pass bands, complete or nearly complete attenuation of the noise artifact may be achieved.

An alternative embodiment is depicted in FIG. 5a wherein the patient's heart rate (in this example 36 BPM) may be below a predetermined threshold. The threshold is not to be limited by the present example, but in embodiments may be established at any heart rate within the range of potential patient heart rates. In the embodiment depicted in FIG. 5a a single pass band 69 is used; however, the single pass band 69 includes each of the determined heart rate frequency harmonics. The signal pass band 69 may be centered on the entire group of heart rate harmonic frequencies. In the present example of FIG. 5a, ECG data with a heart rate of 36 will have a fundamental frequency at 0.6 Hz, a first harmonic at 1.2 Hz, and a second harmonic at 1.8 Hz. Therefore, the single pass band 69 may be centered at the average value of the determined harmonic frequencies, or 1.2 Hz. As a further example, if only the fundamental frequency (0.6 Hz) and the first harmonic frequency (1.2 Hz) were used, then the single pass band may be centered at 0.9 Hz.

The single pass band 69 therefore still exhibits adaptive filtering characteristics at the center frequency as well as the cut off frequencies are still determined by the patient's heart rate associated with the ECG data.

Referring back to FIG. 3, the data processing system 50 therefore produces a filtered frequency domain signal from each of the frequency domain filters: the fundamental frequency filter 58, the first harmonic filter 60, and the $n^{th}$ harmonic filter 62. Each of these signals consists of a small band of frequency domain data centered at the aforementioned heart rate harmonic frequencies. These filtered frequency domain signals are all provided to an oscillometric waveform reconstructor 70 that takes the received filtered frequency domain signals and reconstructs a single time domain oscillometric signal. One technique that may be used to reconstruct the time domain oscillometric signal would be an inverse FFT. Due to the relatively small amount of data remaining in the filtered frequency domain signals (as compared to the original frequency domain signal), some embodiments may use simplified data processing techniques to convert the filtered frequency domain signal back into the time domain. The reconstructed oscillometric signal 72 is then provided to an oscillation size calculator 74 that measures the amplitude of the oscillometric pulses in the reconstructed oscillometric signal 72 such that an oscillometric envelope may be constructed using data from that pressure step.

In an alternative embodiment, the data processing system 50 may further include an additional signal processor (not depicted) that performs basic signal processing functions on the acquired raw oscillometric data. These basic signal processing functions may include the prior art technique of bandpass filtering to remove signal data at frequencies well above or well below the desired oscillometric pulse data, oscillometric pulse detrending, or removing any of the DC component of the acquired raw oscillometric signal.

Figure 4:
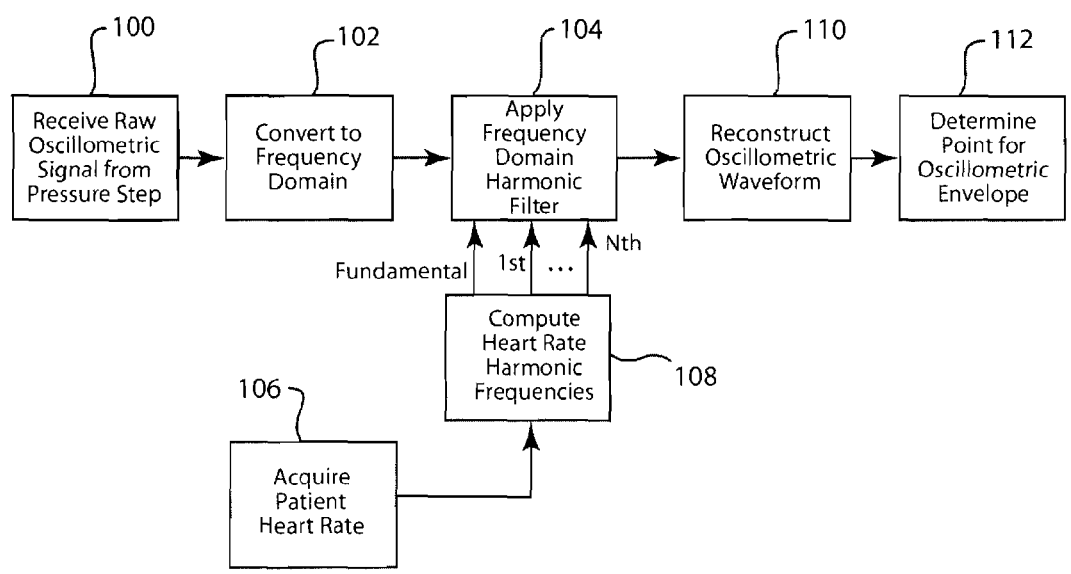
FIG. 4 is a flow chart depicting an embodiment of a method for the artifact resistant analysis of oscillometric data.

FIG. 4 is a flow chart depicting an embodiment of a method of processing an oscillometric signal. The method may begin by receiving a raw oscillometric signal as recorded by a pressure transducer from a pressure step of a pressure controlled cuff at step 100. Next, the oscillometric signal received at step 100 is converted to the frequency domain in step 102. As mentioned above, the conversion from the time domain to the frequency domain of the oscillometric signal in step 102 may be performed by the use of an FFT, the size of which would be determined by the amount of data in the oscillometric signal as dictated by the length of the signal itself as well as the sampling rate at which the signal was acquired.

A frequency domain harmonic filter is applied to the frequency domain oscillometric signal at step 104. The characteristics of the frequency domain harmonic filter are determined by the steps of acquiring the patient's heart rate 106 and using the acquired patient heart rate to compute one or more heart rate harmonic frequencies 108. The computation of at least one harmonic frequency of the patient's heart rate in step 108 may yield results of the heart rate fundamental frequency, heart rate first harmonic frequency and so forth until the patient's $n^{th}$ harmonic frequency is computed. In some embodiments however, only the fundamental frequency, first harmonic, and second harmonic may be necessary to construct one or more frequency domain filters of the desired specificity for the system and method as disclosed herein.

The computed heart rate fundamental and harmonic frequencies from step 108 are used to create the frequency domain harmonic filter that is applied in step 104. While the system and method has been previously described with respect to FIG. 3 as incorporating and applying a plurality of individual frequency domain harmonic filters as described with respect to FIG. 5a, an alternative embodiment may use the heart rate harmonic frequencies computed in step 108 to create a single pass band frequency domain filter whose characteristics (i.e. center and cut-off frequencies) are adaptive to the determined heart rate fundamental and harmonic frequencies.

Regardless as to the structure or data flow of the frequency domain harmonic filter used in step 104 or the results of the application of the frequency domain filter to the frequency domain oscillometric signal in step 104, the filtered frequency domain oscillometric signal must be reconstructed into a time domain oscillometric signal in step 110. There are a variety of well-known techniques for the reconstruction of a time domain signal from a frequency domain signal, such as inverse FFT. It is understood that the filtering performed on the frequency domain oscillometric signal may reduce the complexity of the resulting filtered frequency domain signal such that simplified time domain reconstruction algorithms may be implemented.

Finally, the time domain oscillometric signal reconstructed in step 110 is used to identify oscillometric pulses for the creation of an oscillometric envelope. In some embodiments the newly constructed oscillometric pulses for each pressure step may be individually used as input to further determine the envelope such as finding the maximum oscillation amplitude. In other embodiments, the average value of the amplitudes of the oscillometric pulses at each pressure step may be used as a single representative data point for that pressure step as input to further determine the oscillometric envelope. It may be further noted that in some embodiments the first and last reconstructed oscillation at each pressure step may be eliminated to further improve the determination of the representative data point. After the construction of the oscillometric envelope, the patient's blood pressure estimates may be calculated.

Figure 7A:
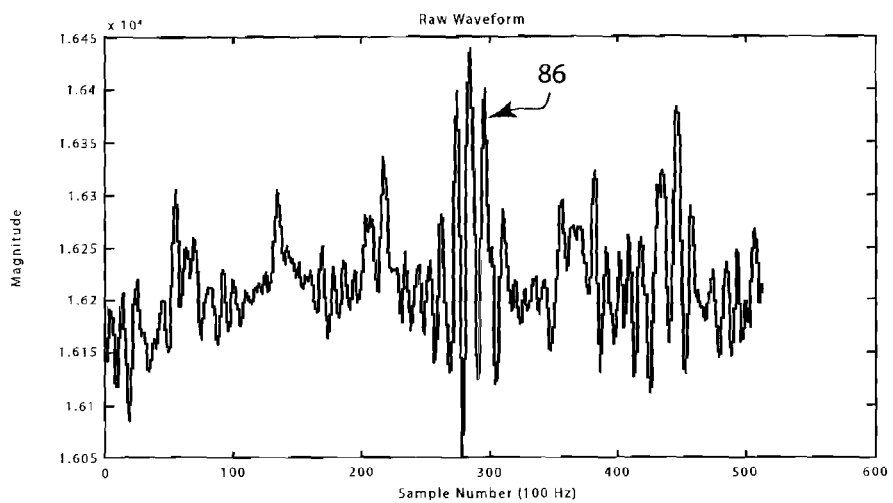
FIG. 7a-7c are graphs depicting the signal processing performed on oscillometric data with a high frequency content artifact.
Figure 7B:
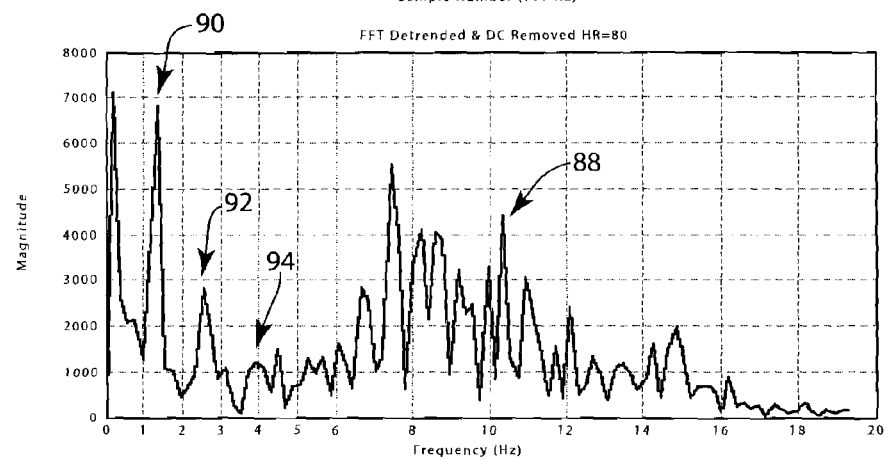
Figure 7C:
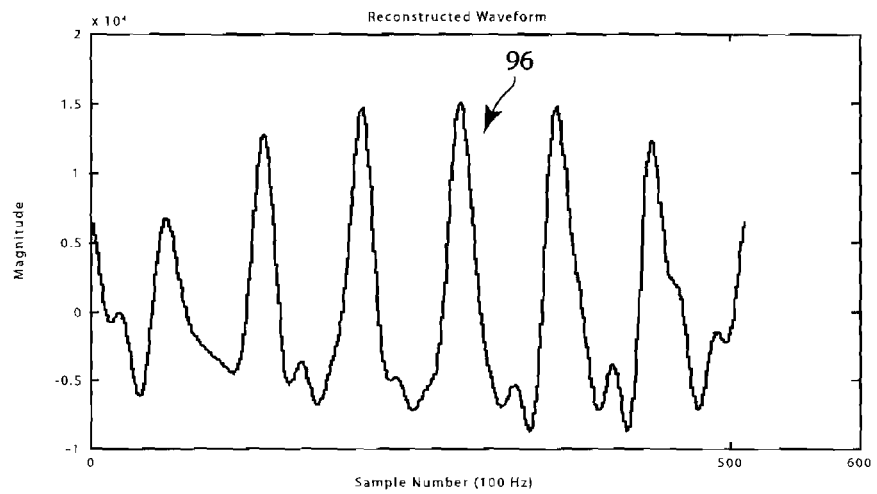
Figure 8A:
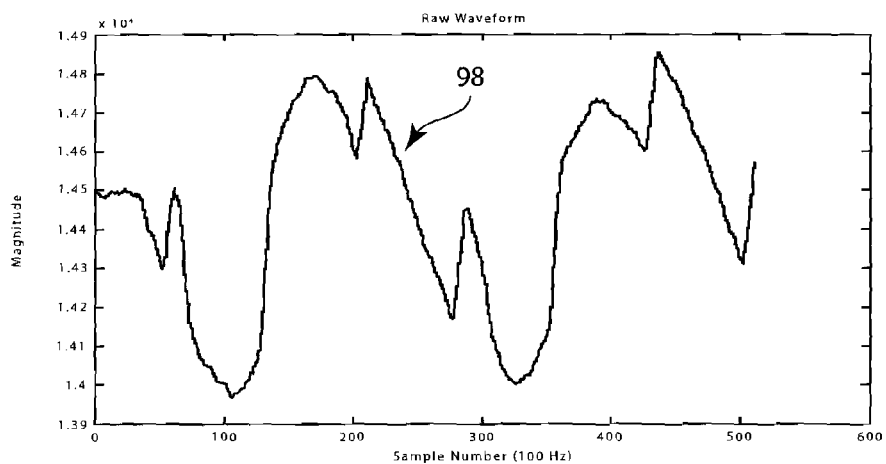
FIGS. 8a-8c are graphs depicting the signal processing performed on oscillometric data with a low frequency content artifact.
Figure 8B:
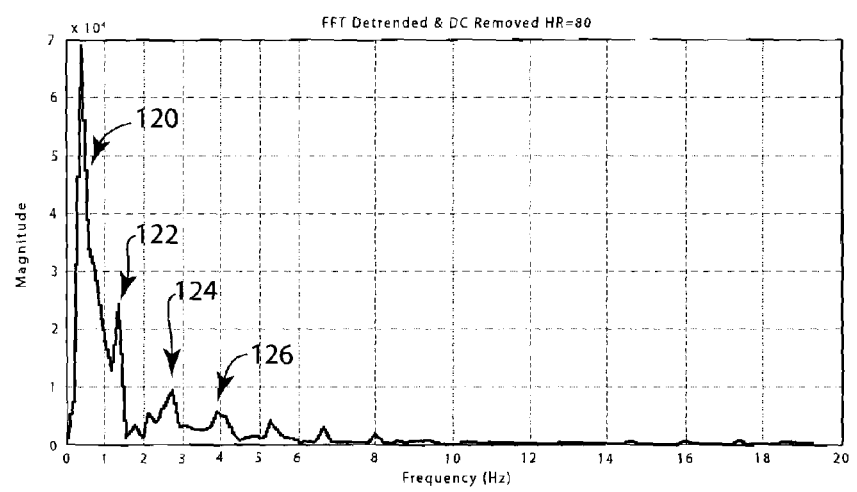
Figure 8C:
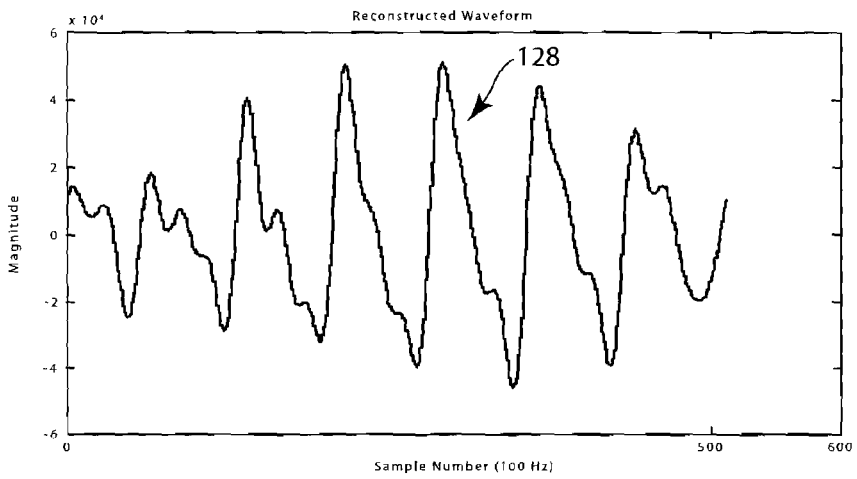

FIGS. 6-8 present graphs of various signals either acquired or created during the implementation of embodiments of the systems and methods as in accordance with the present disclosure. Details regarding embodiments of the presently disclosed system and method may be more particularly described with reference to the graphs of FIGS. 6-8. Each of the FIGS. 6-8 represents a different type of acquired oscillometric signal and thus the signal processing performed under a variety of conditions.

Figure 6A:
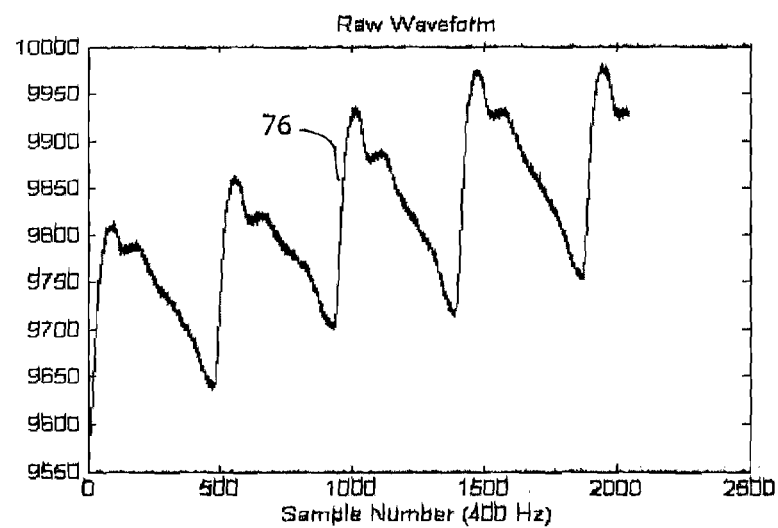
FIGS. 6a-6c are graphs depicting the signal processing performed on generally artifact free oscillometric data.

FIG. 6a depicts a relatively clean or ideal raw oscillometric signal 76. It should be noted that the raw oscillometric signal 76 appears to include a variable DC component. This DC component may be removed through signal processing such as removing a dominant DC component, or by linearly detrending a slowly varying DC component. It should be noted that the raw oscillometric pulse signal has been acquired at a sampling rate of 400 Hz and that for the graph of FIG. 6a, 2,000 data points have been acquired. Therefore, the raw oscillometric pulse signal 76 represents approximately 5 seconds of data of a patient with a heart rate of approximately 54 beats per minute (BPM).

Figure 6B:
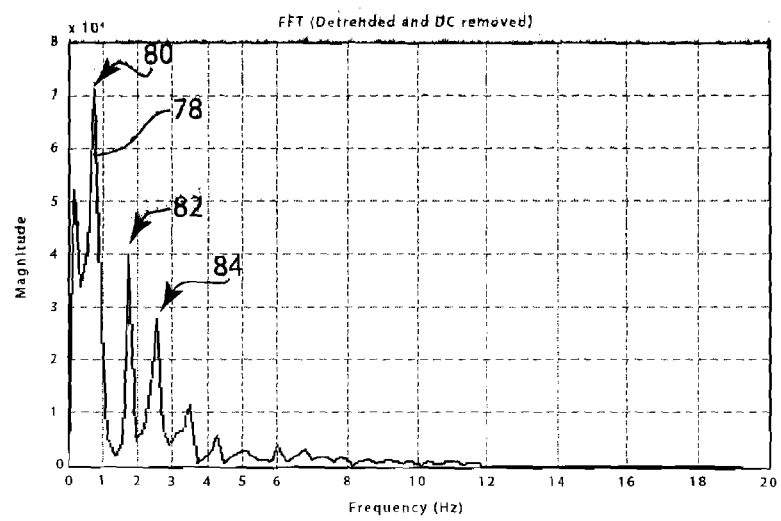

Once the oscillometric signal 76 has undergone DC removal or detrending, the FFT of the resulting signal is calculated. The resulting frequency domain oscillometric signal 78 is depicted in FIG. 6b. The fundamental frequency of the heart rate is the number of heartbeats per second. Furthermore, the $n^{th}$ harmonic frequency is (1+n) times the fundamental frequency. Therefore, for a heart rate of 54 BPM, the fundamental frequency is 0.9 Hz, the first harmonic is at 1.8 Hz and the second harmonic is at 2.7 Hz.

Portions of the frequency domain oscillometric signal 78 can be identified as occurring at the fundamental frequency 80, first harmonic 82 and second harmonic 84. Thus from the depiction of the frequency domain oscillometric signal 78 in FIG. 6b, it can be seen that adaptive frequency domain filtering with pass bands tightly centered on each of the fundamental frequency and at least one harmonic frequency maximizes the passing of data that should be attributed to the oscillometric pulses while removing any other signal data resulting from noise or other artifacts.

Figure 6C:
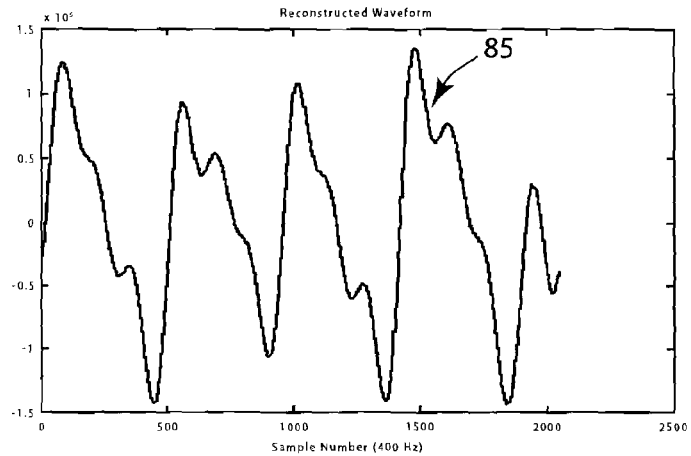

FIG. 6c depicts the reconstructed time domain oscillometric signal 85. A comparison of the oscillometric signal 76 of FIG. 6a to the reconstructed oscillometric signal 85 of FIG. 6c identifies that each oscillometric pulse of the reconstructed signal 85 is of an improved quality compared to that originally acquired. This improved signal quality consequently leads to improved determination of the patient's blood pressure.

FIG. 7a is a raw oscillometric signal 86 that was acquired while the patient was shivering. In comparison to FIG. 6a, the relatively high frequency content of the shiver artifact in the oscillometric signal 86 greatly obscures the oscillometric pulses.

It should be noted that the patient's heart rate associated with the oscillometric signal 86 was determined to be 80 BPM. This could have been determined with a heart rate monitor, or by signal processing applied to the oscillometric signal. In alternative embodiments, the heart rate may be determined from a previous blood pressure determination procedure processing of the ECG signal, or by processing any other physiological signal correlated to heart rates. The heart rate of 80 BPM equates a fundamental frequency of 1.33 Hz and the first and second harmonics are located at 2.67 Hz and 4.0 Hz, respectively. Therefore, in the frequency domain oscillometric signal 88 depicted in FIG. 7b, only the oscillometric data centered about the fundamental frequency 90, first harmonic 92 and second harmonic 94 is desired for the determination of the patient's blood pressure.

As can be seen by a comparison of the raw oscillometric signal 86 of FIG. 7a to the reconstructed signal 96 of FIG. 7c, the reconstructed oscillometric signal 96 provides a greatly enhanced signal for determining not only the location and existence of oscillometric pulses, but the amplitude of each of the oscillometric pulses at the pressure step.

FIG. 8a depicts a raw oscillometric signal 98 wherein the oscillometric pulses have been obscured by a motion artifact due to a patient moving his or her arm. This motion artifact is of a relatively low frequency in comparison to the underlying oscillometric signal and greatly obscures the oscillometric pulses within the raw oscillometric signal 98. Once again it has been determined that the heart rate of the patient is 80 BPM during the collection of the oscillometric signal 98. As the heart rate is 80 BPM, the fundamental frequency, the first harmonic, and the second harmonic all remain the same as with respect to FIG. 7. As with the frequency domain signal 88 of FIG. 7, the frequency domain oscillometric signal 120 in step 8b includes signal data relevant to the determination of the patient's blood pressure centered at the fundamental frequency 122, the first harmonic 124 frequency, and the second harmonic 126 frequency. It should also be noted that while the fundamental, first harmonic, and second harmonic frequencies have been used in this description, the filtering may extend out to the nth harmonic frequency if such is deemed desirable by one skilled in the art.

The filtered frequency domain oscillometric signal is then reconstructed in the time domain to provide oscillometric signal 128 depicted in picture 8c. It is from the reconstructed oscillometric signal 128 that the associated data point of the oscillometric envelope for that particular pressure step may be calculated.

The use of a frequency domain adaptive filtering system and technique that is adaptive to the patient's heart rate produces the benefit of an improved resistance and/or tolerance for artifacts in the originally acquired oscillometric signal. This produces the benefits of decreasing the amount of data to be recorded at each pressure step, reducing noise and artifacts in the oscillometric signal, and improving the overall quality of the oscillometric signal at each pressure step. Often, when an oscillometric signal has artifacts or other noise corrupting the signal, the NIBP system will reject the acquired corrupted data and increases the length of time for the pressure step until an adequate oscillometric signal is acquired. Many techniques are presently available for determining when the acquired oscillometric signal is of a quality sufficient for the determination of the patient's blood pressure. However, the patient experiences discomfort as the length of the NIBP determination procedure increases due to the pressure of the inflated cuff against the patient's arm and the resulting occlusion of the blood flow into and out of the patient's arm by the pressure cuff. Therefore, embodiments of the presently disclosed system and technique enable the use of an oscillometric signal that may otherwise have been rejected as being unfit for the determination of a patient's blood pressure.

The application of an adaptive frequency domain filter improves the quality of the resulting oscillometric signal from which the oscillometric envelope and eventually the patient's blood pressure are estimated. Often, there is significant energy content in the noise at particular frequencies in the raw oscillometric signal. Such targeted areas of high-energy content noise may include low frequencies (less than or equal to 1 Hz) for certain patient motion artifacts, higher frequencies (greater than 7 Hz) for other patient artifacts, or 60 Hz electromagnetic line noise. The use of targeted, adaptive pass band filters allows for frequencies of high noise content to be filtered out while only targeted frequencies known to include oscillometric data are passed through the filter. Thus, improved removal of noise and artifacts is achieved as well as improving the oscillometric data that is passed through the filter. The improved signal quality of the reconstructed oscillometric signal increases the NIBP system's accuracy in computing the patient's blood pressure.

Embodiments of the system and method as disclosed herein may be implemented solely through the use of a computer, such that the computer performs the functions as disclosed with respect to the system and method as disclosed herein. The technical effect of these computer implemented embodiments may be improved accuracy in the determination of a patient's blood pressure as well as reduced blood pressure determination time by reducing the chances that the oscillometric signal from a pressure step would be rejected as being insufficient for the determination of the patient's blood pressure.

This written description uses examples to disclose features of the embodiments, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

What is claimed is:

1. A method of computing an oscillometric envelope for use in determining the blood, pressure of a patient, the method comprising:
   receiving, with a processing unit, an oscillometric signal from a blood pressure cuff connected to a patient;
   acquiring a heart rate from the patient with a heart rate monitor separate from the blood pressure cuff, the heart rate monitor being a different modality from the blood pressure cuff;
   computing the fundamental frequency of the heart rate with a fundamental frequency computer operating on the processing unit;
   computing at least one harmonic frequency of the heart rate with a harmonic frequency computer operating on the processing unit;
   converting the oscillometric signal to a frequency domain oscillometric signal with a time to frequency converter;
   removing acquisition artifacts from the received oscillometric signal by:
   filtering, with the processing unit, the frequency domain oscillometric signal using a band pass filter centered on the fundamental frequency of the heart rate acquired from the heart rate monitor of a different modality to produce a first filtered frequency domain signal;
   filtering, with the processing unit, the frequency domain oscillometric signal using a band pass filter centered on the at least one harmonic frequency of the heart rate acquired from the heart rate monitor of a different modality to produce a second filtered frequency domain signal; and
   reconstructing the oscillometric signal with an oscillometric waveform reconstructor operating on the processing unit from the first and second filtered frequency domain signals to produce a reconstructed oscillometric signal;
   computing at least one oscillometric envelope data point from the reconstructed oscillometric signal with an oscillation size calculator operating on the processing unit;
   computing an oscillometric envelope from the computed at least one oscillometric data point; and
   determining at least one of mean arterial pressure, systolic pressure, and diastolic pressure from the oscillometric envelope.

2. The method of claim 1, wherein the step of converting the oscillometric signal to the frequency domain is performed using a fast Fourier transform (FFT).

3. The method of claim 1, wherein the step of computing at least one harmonic frequency of the heart rate includes computing the first harmonic frequency and the second harmonic frequency.

4. The method of claim 3, further comprising the step of filtering the frequency domain oscillometric signal with a pass band centered at the first harmonic frequency to produce a second filtered frequency domain signal; and
   filtering the frequency domain oscillometric signal with a pass band centered at the second harmonic frequency to produce a third filtered frequency domain signal.

5. The method of claim 1 further comprising the steps of:
   comparing the heart rate of the patient to a predetermined threshold; and if the heart rate of the patient is below the predetermined threshold, filtering the frequency domain oscillometric signal with a single band pass filter that comprises the fundamental frequency and the at least one harmonic frequency.

6. The method of claim 1 wherein the steps of filtering the frequency domain oscillometric signal are performed using a band pass filter of a bandwidth less than or equal to the fundamental frequency centered at the fundamental frequency of the heart rate and a band pass filter of a bandwidth less than or equal to the fundamental frequency centered at least one harmonic frequency.

7. The method of claim 1, wherein the received oscillometric signal is from a single pressure step of the blood pressure cuff signal.

8. The method of claim 7, further comprising repeating the method at a plurality of blood pressure cuff pressure steps to produce a plurality of computed envelope data points.

9. The method of claim 8, wherein the heart rate acquired from the patient with the heart rate monitor is continuously acquired, and further comprising:
calculating at least one new harmonic frequency from the continuously acquired heart rate;
filtering the frequency domain oscillometric signal with band pass filters comprising the at least one new harmonic frequency.

10. The method of claim 6, wherein the step of computing an oscillometric envelope data point further includes removing the first and last reconstructed oscillations and determining an oscillometric envelope data point from the remaining reconstructed oscillations.

11. A system for processing an oscillometric signal from a plurality of pressure steps of a blood pressure cuff to determine the blood pressure of a patient, the oscillometric signal having at least one artifact due to the acquisition of the oscillometric signal with the blood pressure cuff, the system comprising:
a heart rate monitor connected to the patient, wherein the heart rate monitor is a separate modality from the blood pressure cuff, the heart rate monitor acquires the patient's heart rate at each pressure step;
a time-to-frequency domain converter that receives the oscillometric signal acquired at each pressure step and converts the oscillometric data into the frequency domain:
a fundamental frequency computer connected to the heart rate monitor, the fundamental frequency computer deriving a fundamental frequency of the heart rate at each pressure step;
a fundamental frequency filter connected to the time-to-frequency domain converter and the fundamental frequency computer, the fundamental frequency filter comprising a pass band centered at the fundamental frequency of the heart rate at each pressure step, the fundamental frequency filter producing a harmonic frequency filter frequency domain oscillometric signal;
a harmonic frequency computer connected to the heart rate monitor, the harmonic frequency computer deriving at least a harmonic frequency of the heart rate at each pressure step;
a harmonic frequency filter connected to the time-to-frequency domain converter and the harmonic frequency computer, the harmonic frequency filter comprising at least one pass band centered at the harmonic frequency of the heart rate at each pressure step, the harmonic frequency filter producing a harmonic frequency filtered frequency domain oscillometric signal;
a reconstruction calculator that receives the fundamental frequency filtered frequency domain oscillometric signal and the harmonic frequency filtered frequency domain oscillometric signal and reconstructs a time domain oscillometric signal without the at least one artifact from the received filtered frequency domain oscillometric signals;
an oscillometric envelope calculator that processes the time domain oscillometric signal at each pressure step to produce an oscillometric envelope from envelope data points corresponding to each pressure step; and
a blood pressure determination calculator connected to the oscillometric envelope calculator, the blood pressure determination calculator analyzes the oscillometric envelope to determine the blood pressure of the patient.

12. The system of claim 11 wherein the harmonic frequency calculator further derives at least the heart rate first and second harmonic frequencies, and the filter further comprises the first and second harmonic frequencies.

13. The system of claim 12 wherein the filter further comprises pass bands centered at the bean rate fundamental frequency and at least the first and second harmonic frequencies.

14. The system of claim 13 wherein the pass bands centered at the heart rate fundamental frequency and at least the first and second harmonic frequencies are of a bandwidth less than the fundamental frequency.

15. The system of claim 11 further comprising a DC removal calculator, the calculator receiving the oscillometric data and removing the DC component from the oscillometric data.

16. A method of determining a blood pressure of a patient, the method comprising:
operating a blood pressure cuff through a plurality of pressure steps;
acquiring oscillometric signals at each of the a plurality of pressure steps, the oscillometric signals having at least one artifact due to the acquisition of the oscillometric signals with the blood pressure cuff;
acquiring a heart rate of the patient at each pressure step with a heart rate monitor of a separate modality from the blood pressure cuff, each acquired heart rate associated to an oscillometric signal acquired at a same pressure step;
computing the fundamental frequency of each of the acquired heart rates with a fundamental frequency computer operating on a processing unit;
computing at least one harmonic frequency of each of the acquired heart rates with a harmonic frequency computer operating on the processing unit;
converting each of the oscillometric signals to a frequency domain oscillometric signal with a time to frequency converter;
removing acquisition artifacts from each oscillometric signal by:
filtering, with the processing unit, the frequency domain oscillometric signal with a band pass filter centered on the fundamental frequency of the associated heart rate to produce a first filtered frequency domain signal consisting of frequency domain oscillometric data centered at the fundamental frequency of the associated heart rate;
filtering, with the processing unit, the frequency domain oscillometric signal with at least one band pass filter centered on at least one harmonic frequency of the associated heart rate to produce a second filtered frequency domain signal consisting of frequency domain oscillometric data centered at the at least one harmonic frequency of the associated bean rate; and reconstructing the oscillometric signal in the time domain from the first and second filtered frequency domain signals with an oscillometric waveform reconstructor operating on the processing unit to produce a reconstructed oscillometric signal;

computing at least one data point from each of the reconstructed oscillometric signals;

computing an oscillometric envelope from the computed data points; and determining at least one of mean arterial pressure, systolic pressure, and diastolic pressure from the oscillometric envelope.

17. The method of claim 16, wherein the band pass filter centered on the fundamental frequency and the at least one band pass filter centered on at least one harmonic frequency have bandwidths less than or equal to the fundamental frequency.

18. The method of claim 16, further comprising processing the oscillometry signals acquired al each pressure step to remove a dc portion of the oscillometric signal.

* * * * *